US00PP31154P2

(12) United States Plant Patent
Bisschop et al.

(10) Patent No.: US PP31,154 P2
(45) Date of Patent: Dec. 3, 2019

(54) EDELWEISS PLANT NAMED 'ET LP01'

(50) Latin Name: *Leontopodium alpinum*
Varietal Denomination: ET LP01

(71) Applicants: Elisabeth Bisschop, Boijl (NL); Bart Noordhuis, Boijl (NL)

(72) Inventors: Elisabeth Bisschop, Boijl (NL); Bart Noordhuis, Boijl (NL)

(73) Assignee: Eternal Plant Boijl B.V., Boijl (NL)

( * ) Notice: Subject to any disclaimer, the term of this patent is extended or adjusted under 35 U.S.C. 154(b) by 0 days.

(21) Appl. No.: 16/350,471

(22) Filed: Nov. 19, 2018

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1
See application file for complete search history.

(56) References Cited

FOREIGN PATENT DOCUMENTS

QZ PBR 20172958 11/2017

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of Edelweiss plant named 'ET LP01', characterized by its upright and mounded plant habit; freely branching growth habit; freely flowering habit; large inflorescences with pubescent light greyed green-colored involucral bracts; and good inflorescence longevity.

2 Drawing Sheets

Botanical designation: *Leontopodium alpinum.*
Cultivar denomination: 'ET LP01'.

BACKGROUND OF THE INVENTION

The present invention relates to a new and distinct cultivar of Edelweiss plant, botanically known as *Leontopodium alpinum* and hereinafter referred to by the name 'ET LP01'.

The new Edelweiss plant is a product of a planned breeding program conducted by the Inventors in Boijl, The Netherlands. The objective of the breeding program is to create new freely-flowering Edelweiss plants with large and attractive inflorescences supported on strong peduncles.

The new Edelweiss plant originated from a cross-pollination made by the Inventors in Boijl, The Netherlands in July, 2014 of a proprietary selection of *Leontopodium alpinum* identified as code number L.442S, not patented, as the female, or seed parent with a proprietary selection of *Leontopodium alpinum* identified as code number L.164A, not patented, as the male, or pollen, parent. The new Edelweiss plant was discovered and selected by the Inventor as a single flowering plant from within the progeny of the stated cross-pollination in a controlled environment in Boijl, The Netherlands in August, 2015.

Asexual reproduction of the new Edelweiss plant by tissue culture in a controlled greenhouse environment in Boijl, The Netherlands since September, 2015 has shown that the unique features of this new Edelweiss plant are stable and reproduced true to type in successive generations.

SUMMARY OF THE INVENTION

Plants of the new Edelweiss have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ET LP01'. These characteristics in combination distinguish 'ET LP01' as a new and distinct Edelweiss plant:

1. Upright and mounded plant habit.
2. Freely branching growth habit.
3. Freely flowering habit.
4. Large inflorescences with pubescent light greyed green-colored involucral bracts.
5. Good inflorescence longevity.

Plants of the new Edelweiss differ from plants of the female parent selection in the following characteristics:

1. Plants of the new Edelweiss are not as compact as plants of the female parent selection.
2. Inflorescences of plants of the new Edelweiss are longer lasting than inflorescences of plants of the female parent selection.

Plants of the new Edelweiss differ from plants of the male parent selection in the following characteristics:

1. Plants of the new Edelweiss are not as compact as plants of the male parent selection.
2. Plants of the new Edelweiss are more upright than plants of the male parent selection.
3. Inflorescences of plants of the new Edelweiss are longer lasting than inflorescences of plants of the male parent selection.

Plants of the new Edelweiss can be compared to *Edelweiss alpinum* 'Berghman', disclosed in U.S. Plant Pat. No. 29,106. In side-by-side comparisons, plants of the new Edelweiss differ primarily from plants of 'Berghman' in the following characteristics:

1. Plants of the new Edelweiss are not as vigorous as plants of 'Berghman'.
2. Plants of the new Edelweiss have stronger stems than plants of 'Berghman'.
3. Plants of the new Edelweiss have larger inflorescences with more involucral bracts per inflorescence than plants of 'Berghman'.
4. Involucral bracts of plants of the new Edelweiss are light greyed green in color whereas involucral bracts of plants of 'Berghman' are yellow green in color.
5. Peduncles of plants of the new Edelweiss are longer and thicker than peduncles of plants of 'Berghman'.
6. Inflorescences of plants of the new Edelweiss are longer lasting than inflorescences of plants of 'Berghman'.

BRIEF DESCRIPTION OF THE PHOTOGRAPHS

The accompanying photographs illustrate the overall appearance of the new Edelweiss plant showing the colors as true as it is reasonably possible to obtain in colored reproductions of this type. Colors in the photographs may differ slightly from the color values cited in the detailed botanical description which accurately describe the colors of the new Edelweiss plant.

The photograph on the first sheet comprises a side perspective view of a typical flowering plant of 'ET LP01' grown in an outdoor nursery.

The photograph on the second sheet is a close-up view of typical inflorescences of 'ET LP01'.

DETAILED BOTANICAL DESCRIPTION

The aforementioned photographs and following observations, measurements and values describe plants grown in 3-liter containers during the summer and autumn in an outdoor nursery in Boijl, The Netherlands and under cultural conditions typical of commercial Edelweiss plant production. During the production of the plants, day temperatures ranged from 18° C. to 22° C. and night temperatures ranged from 10° C. to 16° C. Plants were one year old when the photographs and the detailed description were taken. In the following description, color references are made to The Royal Horticultural Society Colour Chart, 2001 Edition, except where general terms of ordinary dictionary significance are used.

Botanical classification: *Leontopodium alpinum* 'ET LP01'.

Parentage:

*Female, or seed, parent.*—Proprietary selection of *Leontopodium alpinum* identified as code number L.442S, not patented.

*Male, or pollen, parent.*—Proprietary selection of *Leontopodium alpinum* identified as code number L.164A, not patented.

Propagation:

*Type.*—By in vitro meristem culture.

*Time to initiate roots.*—About seven to eight days at soil temperatures about 15° C. and ambient temperatures about 20° C.

*Time to produce a rooted young plants.*—About four weeks at soil temperatures about 15° C. and ambient temperatures about 20° C.

*Root description.*—Medium in thickness; fleshy; color, close to 162C.

*Rooting habit.*—Freely branching; medium density.

Plant description:

*Plant and growth habit.*—Herbaceous perennial; upright and mounded plant habit; freely branching growth habit with numerous lateral branches developing per plant, dense and bushy appearance; moderately vigorous growth habit; medium growth rate.

*Plant height.*—About 30 cm to 42 cm.

*Plant width.*—About 35 cm to 50 cm.

*Lateral branches (peduncles).*—Length: About 10 cm to 15 cm. Diameter: About 5 mm. Internode length: About 5 mm to 8 mm. Angle: Mostly upright. Strength: Strong. Texture and luster: Pubescent; matte. Color: Close to 147C tinged with close to 183A; pubescence, close to 155C.

Leaf description:

*Arrangement.*—Alternate, simple; sessile.

*Length.*—About 6 cm to 8 cm.

*Width.*—About 0.5 cm to 1 cm.

*Shape.*—Linear to acicular.

*Apex.*—Acute.

*Base.*—Acute.

*Margin.*—Entire.

*Texture and luster, upper and lower surfaces.*—Pubescent; matte.

*Venation pattern.*—Pinnate.

*Color.*—Developing leaves, upper surface: Close to 189A. Developing leaves, lower surface: Close to 191A. Fully expanded leaves, upper surface: Close to 147A; venation, close to 147D. Fully expanded leaves, lower surface: Close to 147B; venation, close to 147D.

Inflorescence description:

*Type and arrangement.*—Composite inflorescence form with tubular disc florets subtended by showy involucral bracts; inflorescences borne on terminal peduncles above the foliar plane on strong peduncles; disc florets and involucral bracts arranged acropetally on a capitulum.

*Fragrance.*—Fragrant, fresh and pleasant.

*Flowering season.*—Plants begin flowering about ten weeks after planting; long flowering period, plants flower continuously during the summer in The Netherlands.

*Inflorescence longevity.*—Good postproduction longevity with inflorescences lasting about eight to ten weeks on the plant; inflorescences persistent.

*Quantity of inflorescences.*—Freely flowering habit, typically about 20 to 30 inflorescences per plant.

*Inflorescence buds.*—Height: About 1 cm to 2 cm. Diameter: About 1 cm to 2 cm. Shape: Ovate to round. Texture and luster: Pubescent; matte. Color: Close to 147A.

*Inflorescences.*—Diameter: About 8 cm to 11 cm. Depth (height): About 2 cm. Diameter of disc: About 0.8 cm to 1 cm. Receptacle height: About 0.8 cm to 1 cm. Receptacle diameter: About 6 mm to 8 mm. Receptacle color: Close to 147A.

*Ray florets.*—Ray floret development has not been observed on plants of the new Edelweiss to date.

*Disc florets.*—Quantity and arrangement: Typically more than 20 disc florets per inflorescence massed at center of receptacle. Length: About 0.8 cm to 1 cm. Width: About 2 mm to 4 mm. Shape: Tubular, elongated. Apex: Truncate, recurved. Texture and luster: Smooth, glabrous; velvety; slightly glossy.

Color: When opening, inner and outer surfaces: Close to 149D. Fully opened, inner and outer surfaces: Close to 149B.

*Involucral bracts* (*phyllaries*).—Quantity and arrangement: Typically about 16 to 22 per inflorescence arranged in about three to four whorls subtending the disc florets. Length: About 2 cm to 6 cm. Width: About 4 mm to 8 mm. Shape: Linear. Apex: Obtuse. Base: Peltate. Margin: Entire. Aspect: Mostly straight to somewhat curved. Texture and luster, upper and lower surfaces: Pubescent; fluffy; matte. Color: When opening, upper surface: Close to 192A. When opening, lower surface: Close to 193A. Fully opened, upper and lower surfaces: Close to 192A; color does not change with development.

*Reproductive organs*.—Androecium (present disc florets): Quantity per floret: Typically about 40. Filament length: About 3 mm to 4 mm. Filament color: Close to 165A. Anther shape: Roughly ovoid. Anther size: About 2 mm by 2 mm. Anther color: Close to 187A. Pollen amount: Scarce. Pollen color: Close to 4B. Gynoecium (present on disc florets): Pistil length: About 1 cm to 2 cm. Stigma diameter: About 5 mm. Stigma shape: Star-shaped. Style length: About 1 cm to 2 cm. Style color: Close to 175A. Ovary color: Close to 149B.

*Seeds and fruits*.—To date, seed and fruit production has not been observed on plants of the new Edelweiss.

Disease & pest resistance: To date, plants of the new Edelweiss have not been observed to be resistant to pathogens and pests common to Edelweiss plants.

Garden performance: Plants of the new Edelweiss have been observed to have good garden performance and to tolerate wind, rain and temperatures from about −10° C. to about 35° C.

It is claimed:

1. A new and distinct Edelweiss plant named 'ET LP01' as illustrated and described.

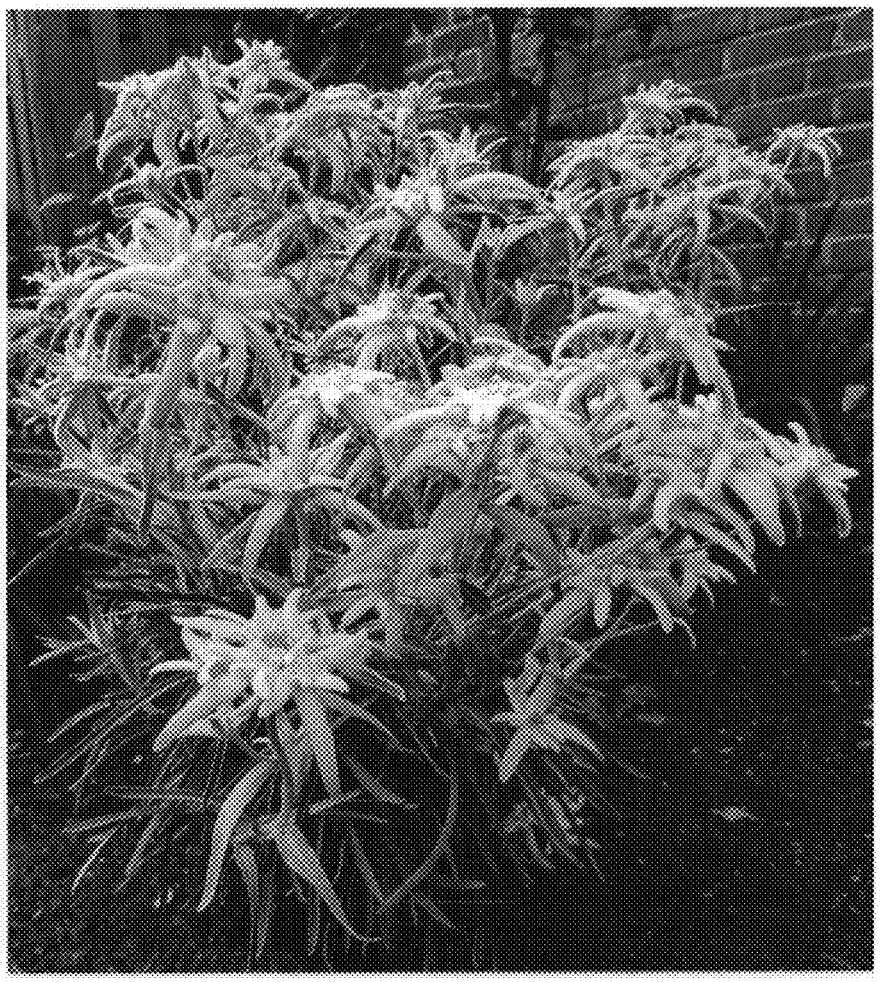

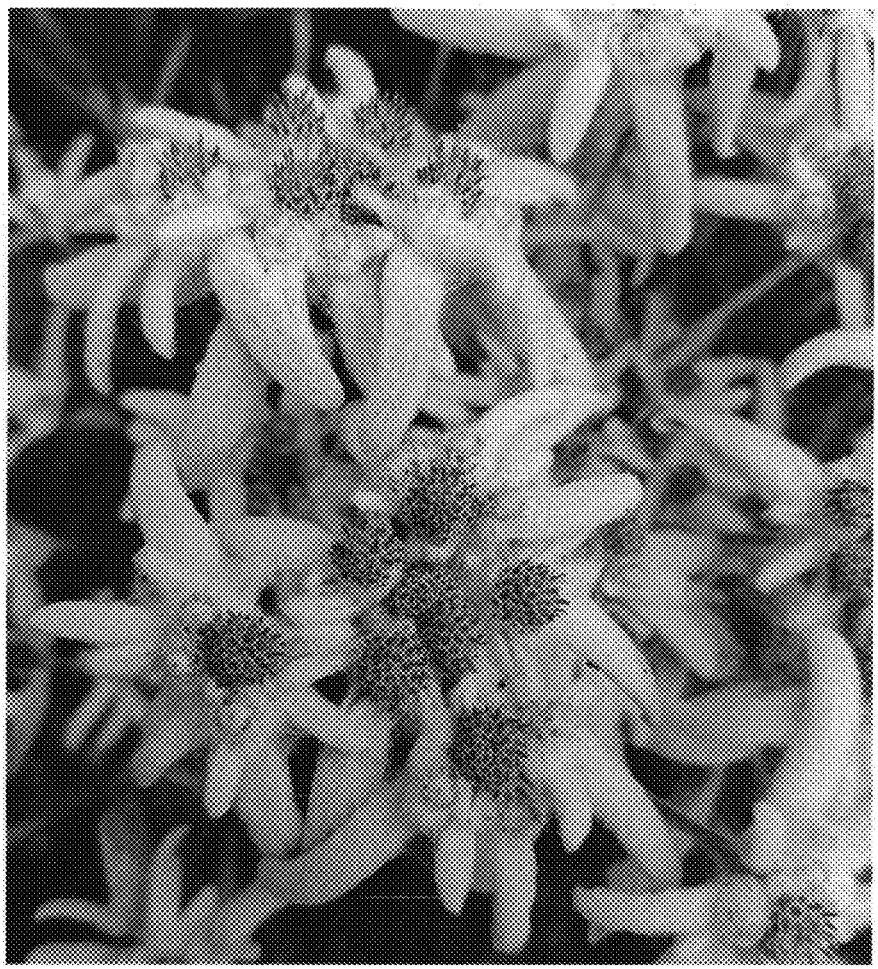

* * * * *